US008105351B2

(12) United States Patent
Lehman et al.

(10) Patent No.: US 8,105,351 B2
(45) Date of Patent: Jan. 31, 2012

(54) METHOD OF PROMOTING TISSUE ADHESION

(75) Inventors: Glen Lehman, Indianapolis, IN (US); Charles J. Filipi, Omaha, NE (US)

(73) Assignee: C.R. Bard, Inc., Murray Hill, NJ (US)

( * ) Notice: Subject to any disclaimer, the term of this patent is extended or adjusted under 35 U.S.C. 154(b) by 1835 days.

(21) Appl. No.: 10/275,521

(22) PCT Filed: May 18, 2001

(86) PCT No.: PCT/US01/40766
§ 371 (c)(1),
(2), (4) Date: Jun. 5, 2003

(87) PCT Pub. No.: WO01/89370
PCT Pub. Date: Nov. 29, 2001

(65) Prior Publication Data
US 2004/0034371 A1 Feb. 19, 2004

Related U.S. Application Data

(60) Provisional application No. 60/205,742, filed on May 19, 2000.

(51) Int. Cl.
*A61B 17/08* (2006.01)
(52) U.S. Cl. ......... 606/213; 606/139; 606/151; 606/232
(58) Field of Classification Search .................. 606/213, 606/49–52, 153, 139, 144, 148, 214, 151; 128/898
See application file for complete search history.

(56) References Cited

U.S. PATENT DOCUMENTS

| 453,508 A | 6/1891 | Ruby |
| 730,152 A | 6/1903 | Pitner |
| 979,342 A | 12/1910 | Schaefer |
| 1,325,699 A | 12/1919 | Oesterhaus |

(Continued)

FOREIGN PATENT DOCUMENTS
DE 3909999 A1 9/1990
(Continued)

OTHER PUBLICATIONS

S. Sherman et al., "Efficacy of Endoscopic Sphincterotomy and Surgical Sphincteroplasty for Patients with Sphincter of Oddi Dysfunction: Randomized, Prospective Study", *Gastrointest Endosc*, vol. 37, No. 2, 1991, p. 249 (Abstract).

(Continued)

*Primary Examiner* — Gary Jackson
*Assistant Examiner* — Diane Yabut
(74) *Attorney, Agent, or Firm* — Wolf, Greenfield & Sacks, P.C.

(57) ABSTRACT

The present invention provides methods and devices for promoting tissue adhesion, which utilizes the healing process and scar tissue formation to bond two tissue surfaces together. A tissue injury is accomplished by destroying the mucosal layer of tissue. After the injury is initiated, the tissue is preferably held in close contact by a tissue apposition means such as a suture, staple or clip device placed adjacent to the treatment site. The tissue injury may be initiated by electrical/radiofrequency energy or chemical or mechanical means integrated with the tissue apposition device or delivered by a separate instrument such as an electrocautery catheter through an endoscope. As scar tissue created by the injury forms, the tissue surfaces become bonded together in a permanent union.

21 Claims, 13 Drawing Sheets

U.S. PATENT DOCUMENTS

| | | |
|---|---|---|
| 1,868,308 A | 7/1932 | Brumfield |
| 2,170,599 A | 8/1939 | Stricklen |
| 2,587,364 A | 2/1952 | Mitchell |
| 2,601,852 A | 7/1952 | Wendt |
| 2,621,655 A | 12/1952 | Olson |
| 2,650,593 A | 9/1953 | Weil et al. |
| 2,880,728 A | 4/1959 | Rights |
| 3,013,559 A | 12/1961 | Thomas |
| 3,238,941 A | 3/1966 | Klein et al. |
| 3,470,875 A | 10/1969 | Johnson |
| 3,716,058 A | 2/1973 | Tanner |
| 3,757,781 A | 9/1973 | Smart |
| 3,760,810 A | 9/1973 | Hoorn |
| 3,845,771 A | 11/1974 | Vise |
| 3,845,772 A | 11/1974 | Smith |
| 3,858,571 A | 1/1975 | Rudolph |
| 4,126,124 A | 11/1978 | Miller |
| 4,144,876 A | 3/1979 | Deleo |
| 4,164,225 A | 8/1979 | Johnson et al. |
| 4,210,148 A | 7/1980 | Stivala |
| 4,216,777 A | 8/1980 | Pridemore |
| 4,226,239 A | 10/1980 | Polk et al. |
| 4,234,111 A | 11/1980 | Dischinger |
| 4,236,470 A | 12/1980 | Stenson |
| 4,291,698 A | 9/1981 | Fuchs et al. |
| 4,345,601 A | 8/1982 | Fukunda |
| 4,414,908 A | 11/1983 | Eguchi et al. |
| 4,415,092 A | 11/1983 | Boyer |
| 4,440,171 A | 4/1984 | Nomoto et al. |
| 4,469,101 A | 9/1984 | Coleman et al. |
| 4,474,174 A | 10/1984 | Petruzzi |
| 4,493,319 A | 1/1985 | Polk et al. |
| D279,504 S | 7/1985 | Tump |
| 4,597,390 A | 7/1986 | Mulhollan et al. |
| 4,607,620 A | 8/1986 | Storz |
| 4,615,472 A | 10/1986 | Nash |
| 4,621,640 A | 11/1986 | Mulhollan et al. |
| 4,637,816 A | 1/1987 | Mann |
| 4,665,906 A | 5/1987 | Jervis |
| 4,672,979 A | 6/1987 | Pohndorf |
| 4,706,653 A | 11/1987 | Yamamoto |
| 4,721,103 A | 1/1988 | Freedland |
| 4,735,194 A | 4/1988 | Stiegmann |
| 4,738,255 A | 4/1988 | Goble et al. |
| 4,741,330 A | 5/1988 | Hayhurst |
| 4,759,364 A | 7/1988 | Boebel |
| 4,794,911 A | 1/1989 | Okada |
| 4,825,259 A | 4/1989 | Berry, Jr. |
| 4,841,888 A | 6/1989 | Mills et al. |
| 4,860,746 A | 8/1989 | Yoon |
| 4,890,615 A | 1/1990 | Caspari et al. |
| 4,898,156 A | 2/1990 | Gatturna et al. |
| 4,899,743 A | 2/1990 | Nicholson et al. |
| 4,923,461 A | 5/1990 | Caspari et al. |
| 4,927,428 A | 5/1990 | Richards |
| 4,932,962 A | 6/1990 | Yoon et al. |
| 4,936,823 A | 6/1990 | Colvin et al. |
| 4,946,468 A | 8/1990 | Li |
| 4,950,285 A | 8/1990 | Wilk |
| 4,968,315 A | 11/1990 | Gatturna |
| 5,002,042 A | 3/1991 | Okada |
| 5,002,550 A | 3/1991 | Li |
| 5,037,021 A | 8/1991 | Mills et al. |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,078,731 A | 1/1992 | Hayhurst |
| 5,080,663 A | 1/1992 | Mills et al. |
| 5,100,417 A | 3/1992 | Cerier et al. |
| 5,100,418 A | 3/1992 | Yoon et al. |
| 5,100,421 A | 3/1992 | Christoudias |
| 5,102,421 A | 4/1992 | Anspach et al. |
| 5,116,349 A | 5/1992 | Aranyi |
| 5,123,913 A | 6/1992 | Wilk et al. |
| 5,125,553 A | 6/1992 | Oddsen et al. |
| 5,147,379 A | 9/1992 | Sabbaghian et al. |
| 5,152,769 A | 10/1992 | Baber |
| 5,163,945 A | 11/1992 | Ortiz et al. |
| 5,171,251 A | 12/1992 | Bregen et al. |
| 5,176,682 A | 1/1993 | Chow |
| 5,193,525 A | 3/1993 | Silverstein et al. |
| 5,199,566 A | 4/1993 | Ortiz et al. |
| 5,203,863 A | 4/1993 | Bidoia |
| 5,207,679 A | 5/1993 | Li |
| 5,207,690 A | 5/1993 | Rohrbacher |
| 5,207,694 A | 5/1993 | Broome |
| 5,211,650 A | 5/1993 | Node |
| 5,213,093 A | 5/1993 | Swindle |
| 5,217,486 A | 6/1993 | Rice et al. |
| 5,220,928 A | 6/1993 | Oddsen |
| 5,224,946 A | 7/1993 | Hayhurst et al. |
| 5,236,445 A | 8/1993 | Hayhurst et al. |
| 5,242,431 A | 9/1993 | Kristiansen |
| 5,254,126 A | 10/1993 | Filipi et al. |
| 5,258,015 A | 11/1993 | Li et al. |
| 5,258,016 A | 11/1993 | Dipoto et al. |
| 5,259,366 A | 11/1993 | Reydel et al. |
| 5,268,001 A | 12/1993 | Nicholson et al. |
| 5,269,789 A | 12/1993 | Chin et al. |
| 5,269,809 A | 12/1993 | Hayhurst et al. |
| 5,273,053 A | 12/1993 | Pohndorf |
| 5,281,236 A | 1/1994 | Bagnato et al. |
| 5,281,237 A | 1/1994 | Gimpelson |
| 5,282,832 A | 2/1994 | Toso et al. |
| 5,284,485 A | 2/1994 | Kammerer et al. |
| 5,290,296 A | 3/1994 | Phillips |
| 5,290,297 A | 3/1994 | Phillips |
| 5,297,536 A | 3/1994 | Wilk |
| 5,304,184 A | 4/1994 | Hathaway et al. |
| 5,306,280 A | 4/1994 | Bregen et al. |
| 5,306,309 A | 4/1994 | Wagner et al. |
| 5,312,438 A | 5/1994 | Johnson |
| 5,320,630 A | 6/1994 | Ahmed |
| 5,324,308 A | 6/1994 | Pierce |
| 5,330,442 A | 7/1994 | Green et al. |
| 5,330,486 A | 7/1994 | Wilk |
| 5,333,624 A | 8/1994 | Tovey |
| 5,334,200 A | 8/1994 | Johnson |
| 5,336,229 A | 8/1994 | Nods |
| 5,344,060 A | 9/1994 | Gravener et al. |
| 5,354,298 A | 10/1994 | Lee et al. |
| 5,356,413 A | 10/1994 | Martins et al. |
| 5,356,416 A | 10/1994 | Chu et al. |
| 5,364,407 A | 11/1994 | Poll |
| 5,364,408 A | 11/1994 | Gordon |
| 5,368,599 A | 11/1994 | Hirsch et al. |
| 5,368,601 A | 11/1994 | Sauer et al. |
| 5,370,662 A | 12/1994 | Stone et al. |
| 5,372,599 A | 12/1994 | Martins |
| 5,372,604 A | 12/1994 | Trott |
| 5,376,101 A | 12/1994 | Green et al. |
| 5,380,334 A | 1/1995 | Torrie et al. |
| 5,383,905 A | 1/1995 | Golds et al. |
| 5,389,103 A | 2/1995 | Melzer et al. |
| 5,391,173 A | 2/1995 | Wilk |
| 5,391,176 A | 2/1995 | Torre |
| 5,391,182 A | 2/1995 | Chin |
| 5,398,844 A | 3/1995 | Zaslavsky et al. |
| 5,403,346 A | 4/1995 | Loeser |
| 5,403,348 A | 4/1995 | Bonutti |
| 5,405,354 A | 4/1995 | Sarrett |
| 5,405,359 A | 4/1995 | Pierce |
| 5,409,499 A | 4/1995 | Yi |
| 5,411,506 A | 5/1995 | Golbe et al. |
| 5,411,522 A | 5/1995 | Trott |
| 5,411,523 A | 5/1995 | Goble |
| 5,413,585 A | 5/1995 | Pagedasa |
| 5,417,691 A | 5/1995 | Hayhurst |
| 5,417,697 A | 5/1995 | Wilk et al. |
| 5,417,699 A | 5/1995 | Klein et al. |
| 5,423,834 A | 6/1995 | Ahmed |
| 5,423,860 A | 6/1995 | Lizardi et al. |
| 5,431,639 A | 7/1995 | Shaw |
| 5,431,666 A | 7/1995 | Sauer et al. |
| 5,433,722 A | 7/1995 | Sharpe et al. |
| 5,437,680 A | 8/1995 | Yoon |

| | | |
|---|---|---|
| 5,439,467 A | 8/1995 | Benderev et al. |
| 5,443,482 A | 8/1995 | Stone et al. |
| 5,445,167 A | 8/1995 | Yoon et al. |
| 5,447,512 A | 9/1995 | Wilson et al. |
| 5,458,608 A | 10/1995 | Wortrich |
| 5,462,545 A | 10/1995 | Wang et al. |
| 5,462,558 A | 10/1995 | Kolesa et al. |
| 5,462,559 A | 10/1995 | Ahmed |
| 5,462,561 A | 10/1995 | Voda |
| 5,464,426 A | 11/1995 | Bonutti |
| 5,466,241 A | 11/1995 | Leroy et al. |
| 5,470,337 A | 11/1995 | Moss |
| 5,474,572 A | 12/1995 | Hayhurst |
| 5,474,573 A | 12/1995 | Hatcher |
| 5,478,353 A | 12/1995 | Yoon |
| 5,487,746 A | 1/1996 | Yu et al. |
| 5,507,754 A | 4/1996 | Green et al. |
| 5,507,758 A | 4/1996 | Thomason et al. |
| 5,507,797 A | 4/1996 | Suzuki et al. |
| 5,514,159 A | 5/1996 | Matula et al. |
| 5,520,700 A | 5/1996 | Beyar et al. |
| 5,520,702 A | 5/1996 | Sauer et al. |
| 5,520,703 A | 5/1996 | Essig et al. |
| 5,527,318 A | 6/1996 | McGarry |
| 5,531,763 A | 7/1996 | Mastri et al. |
| 5,542,432 A | 8/1996 | Slater |
| 5,545,170 A | 8/1996 | Hart |
| 5,545,180 A | 8/1996 | Le et al. |
| 5,549,617 A | 8/1996 | Green et al. |
| 5,562,686 A | 10/1996 | Sauer et al. |
| 5,562,689 A | 10/1996 | Green et al. |
| 5,562,720 A | 10/1996 | Stern et al. |
| 5,569,274 A | 10/1996 | Rapacki et al. |
| 5,569,305 A | 10/1996 | Bonutti |
| 5,571,116 A * | 11/1996 | Bolanos et al. ............... 606/139 |
| 5,582,609 A | 12/1996 | Swanson et al. |
| 5,584,861 A | 12/1996 | Swain et al. |
| 5,584,862 A | 12/1996 | Bonutti |
| 5,591,177 A | 1/1997 | Lehrer |
| 5,591,180 A | 1/1997 | Hinchliffe |
| 5,601,530 A | 2/1997 | Neilsen et al. |
| 5,601,571 A | 2/1997 | Moss |
| 5,609,597 A | 3/1997 | Lehrer |
| 5,618,314 A | 4/1997 | Harwin et al. |
| 5,624,453 A | 4/1997 | Ahmed |
| 5,626,590 A | 5/1997 | Wilk |
| 5,630,824 A | 5/1997 | Hart |
| 5,645,553 A | 7/1997 | Kolesa et al. |
| 5,658,313 A | 8/1997 | Thal et al. |
| 5,665,109 A * | 9/1997 | Yoon ........................ 606/232 |
| 5,665,112 A | 9/1997 | Thal |
| 5,681,328 A | 10/1997 | Lamport et al. |
| 5,681,351 A | 10/1997 | Jamiolkowski et al. |
| 5,683,417 A | 11/1997 | Cooper |
| 5,683,419 A | 11/1997 | Thal |
| 5,683,464 A | 11/1997 | Wagner et al. |
| 5,688,270 A * | 11/1997 | Yates et al. ...................... 606/51 |
| 5,693,060 A | 12/1997 | Martin |
| 5,695,505 A | 12/1997 | Yoon |
| 5,697,940 A | 12/1997 | Chu et al. |
| 5,702,397 A | 12/1997 | Goble et al. |
| 5,720,765 A | 2/1998 | Thal |
| 5,728,136 A | 3/1998 | Thal |
| 5,730,747 A | 3/1998 | Ek et al. |
| 5,735,793 A | 4/1998 | Takahashi et al. |
| 5,735,877 A | 4/1998 | Pagedes |
| 5,741,281 A | 4/1998 | Martin |
| 5,741,301 A | 4/1998 | Pagedes |
| 5,752,963 A | 5/1998 | Allard et al. |
| 5,755,730 A | 5/1998 | Swain et al. |
| 5,782,776 A | 7/1998 | Hani |
| 5,788,715 A | 8/1998 | Watson, Jr. et al. |
| 5,792,153 A | 8/1998 | Swain et al. |
| 5,810,853 A | 9/1998 | Yoon |
| 5,810,854 A | 9/1998 | Beach |
| 5,814,056 A | 9/1998 | Prosst et al. |
| 5,827,298 A | 10/1998 | Hart et al. |
| 5,827,306 A | 10/1998 | Yoon |
| 5,853,416 A | 12/1998 | Tolkoff |
| 5,860,946 A | 1/1999 | Hofstatter |
| 5,897,487 A | 4/1999 | Ouchi |
| 5,899,921 A | 5/1999 | Caspari et al. |
| 5,902,321 A | 5/1999 | Casperi et al. |
| 5,910,105 A | 6/1999 | Swain et al. |
| 5,919,208 A | 7/1999 | Valenti |
| RE36,289 E | 8/1999 | Le et al. |
| 5,931,844 A | 8/1999 | Thompson et al. |
| 5,935,149 A | 8/1999 | Ek |
| 5,938,586 A | 8/1999 | Wilk et al. |
| 5,947,983 A | 9/1999 | Solar et al. |
| 5,972,001 A | 10/1999 | Yoon |
| 5,984,917 A | 11/1999 | Fleischman et al. |
| 5,997,556 A | 12/1999 | Tanner |
| 6,001,110 A | 12/1999 | Adams |
| 6,007,551 A | 12/1999 | Peifer et al. |
| 6,010,515 A | 1/2000 | Swain et al. |
| 6,010,525 A | 1/2000 | Bonutti et al. |
| 6,015,428 A | 1/2000 | Padedas |
| 6,024,755 A | 2/2000 | Addis |
| 6,044,846 A * | 4/2000 | Edwards ........................ 128/898 |
| 6,059,719 A | 5/2000 | Yamamoto et al. |
| 6,059,798 A | 5/2000 | Tolkoff |
| 6,066,160 A | 5/2000 | Colvin et al. |
| 6,071,233 A | 6/2000 | Ishikawa et al. |
| 6,071,292 A | 6/2000 | Makower et al. |
| 6,074,401 A | 6/2000 | Gardiner et al. |
| 6,086,600 A | 7/2000 | Kortenbach |
| 6,086,608 A | 7/2000 | Ek et al. |
| 6,099,535 A | 8/2000 | Lamport et al. |
| 6,126,677 A | 10/2000 | Ganaja et al. |
| 6,129,661 A | 10/2000 | Iafrati et al. |
| 6,136,009 A | 10/2000 | Mears |
| 6,149,658 A | 11/2000 | Gardiner et al. |
| 6,159,234 A | 12/2000 | Bonutti et al. |
| 6,200,329 B1 | 3/2001 | Fung et al. |
| 6,241,140 B1 | 6/2001 | Adams et al. |
| 6,280,452 B1 | 8/2001 | Mears |
| 6,358,259 B1 | 3/2002 | Swain et al. |
| 6,363,937 B1 * | 4/2002 | Hovda et al. ................... 128/898 |
| 6,402,744 B2 * | 6/2002 | Edwards et al. ................. 606/41 |
| 6,436,108 B1 | 8/2002 | Mears |
| 6,514,265 B2 | 2/2003 | Ho et al. |
| 6,551,332 B1 | 4/2003 | Nguyen et al. |
| 6,607,541 B1 | 8/2003 | Gardiner et al. |
| 6,629,630 B2 | 10/2003 | Adams |
| 6,666,844 B1 | 12/2003 | Igo et al. |
| 6,719,763 B2 | 4/2004 | Chung et al. |
| 6,736,828 B1 | 5/2004 | Adams et al. |
| 7,083,615 B2 | 8/2006 | Peterson et al. |
| 7,794,461 B2 | 9/2010 | Eder et al. |
| 2002/0177847 A1 | 11/2002 | Long et al. |
| 2003/0167062 A1 * | 9/2003 | Gambale et al. ............... 606/138 |
| 2003/0171651 A1 | 9/2003 | Page et al. |
| 2003/0171760 A1 | 9/2003 | Gambale et al. |
| 2003/0176880 A1 | 9/2003 | Long et al. |
| 2003/0208209 A1 | 11/2003 | Gambale et al. |
| 2003/0236535 A1 | 12/2003 | Onuki et al. |
| 2004/0034371 A1 | 2/2004 | Lehman et al. |
| 2004/0138704 A1 | 7/2004 | Gambale et al. |
| 2004/0158125 A1 | 8/2004 | Aznoian et al. |
| 2005/0033319 A1 | 2/2005 | Gambale et al. |

FOREIGN PATENT DOCUMENTS

| | | |
|---|---|---|
| EP | 0 591991 A2 | 4/1994 |
| EP | 0 598219 A2 | 5/1994 |
| GB | 2165559 | 4/1986 |
| JP | 10-500318 | 3/1994 |
| JP | 7-136177 | 5/1995 |
| WO | 95/25468 | 3/1994 |
| WO | WO 96/09796 | 4/1996 |
| WO | WO 96/20647 | 7/1996 |
| WO | WO 99/22650 | 5/1999 |
| WO | WO 99/52423 A1 | 10/1999 |
| WO | WO 99/59486 A2 | 11/1999 |
| WO | WO 99/66844 | 12/1999 |
| WO | WO 9966844 A1 * | 12/1999 |
| WO | 01/66018 A1 | 9/2001 |
| WO | WO 01/66001 | 9/2001 |

| WO | WO 01/66018 | 9/2001 |
| WO | 01/89370 A2 | 11/2001 |
| WO | WO 01/87144 | 11/2001 |
| WO | WO 01/89370 | 11/2001 |
| WO | WO 01/89393 | 11/2001 |

OTHER PUBLICATIONS

S. Sherman et al., "Endoscopic Sphincterotomy Induced Hemorrhage: Treatment with Multipolar Electrocoagulation", *Gastrointest Endosc*, vol. 37, No. 2, 1991, p. 249 (Abstract).

G. Lehman et al., "Endoscopic Gastroesophageal Suturing: Does Addition of Cautery Aid Plication Persistence?" *Digestive Disease Week* Poster Board Presentation—May 2000, On-line Abstract Feb. 2000.

C. J. Filipi, Transoral, Flexible Endoscopic Suturing for Treatment of GERD: A Multicenter Trial, *Gastrointest Endosc* Apr. 2001; 53 (4): 416-422.

T. Martinez-Serna et al., Endoscopic Valvuloplasty for GERD, *Gastrointest Endosc* Nov. 2000; 52 (5): 663-70.

Bard Interventional Products Division, C. R. Bard, Inc., "RapidFire™ Multiple Band Ligator—Information for Use", No. AE1904601/01, Issued Jun. 1996.

Cook® Wilson-Cook Medical GI Endoscopy, Sales Literature, www.wilsoncook.com.

Communication pursuant to Article 94(3) EPC for European Application No. 01 933 445, dated Mar. 9, 2010 (4 pages).

Supplementary European Search Report (3 pages).

* cited by examiner

METHOD OF PROMOTING TISSUE ADHESION

CROSS REFERENCE TO RELATED APPLICATIONS

This application is the U.S. National stage of International Application No. PCT/US01/40766, filed on May 18, 2001, published in English, which claims the benefit of U.S. Provisional Application No. 60/205,742, filed on May 19, 2000. The entire teachings of the above application(s) are incorporated herein by reference.

FIELD OF THE INVENTION

The present invention relates to methods of treating tissue of the human body, specifically, methods of promoting adhesion between tissue surfaces.

BACKGROUND OF THE INVENTION

Securely joining one tissue portion to another is important to the successful treatment of various medical ailments. However, because tissue is soft, pliable, and moist and is often subject to dynamic movement, it can be difficult to maintain different segments of tissue joined together. Common methods for joining tissue segments together include: suturing with surgical thread secured by a surgical knot, lock device or application of surgical staples. The success of knotted sutures is dependent on the skill of the physician forming a strong surgical knot. Both stapling and suturing are susceptible to failure if the tissue surrounding the suture or staple tears permitting the material to break free and release the tissue.

Another method for retaining segments of tissue together involves the application of adhesive. Adhesives may be applied in connection with a reinforcing substrate that is flexible, such as a bandage or flexible strip. Alternatively, the adhesive may be applied directly to the tissue folds. Biologically safe tissue adhesives are sometimes used in surgical applications to help maintain tissues joined together. However, the moist pliable nature of tissue makes successfully bonding tissue surfaces together difficult. The bonding agent may not adhere to the tissue surface in the presence of biological fluids, etc. Additionally, the dynamic environments in which most tissue areas exist tend to weaken bonds created by adhesives.

Adhering tissue layers together can be challenging in both external treatment sites as well as internal treatment locations. Internally located tissues may be more difficult to bond together because they are more remote and difficult to reach for securement methods, such as suture placement and knot tying. Additionally, internal treatment sites may be exposed to a moist environment of body fluids such as blood or harsh corrosive substances contained within the body that may serve to weaken adhesive bonds or restraining means such as suture or staples.

Joining tissue can be especially challenging in endoscopic tissue apposition procedures. Endoscopic tissue apposition devices are available that can be used in the body of a patient without the need to make an external incision in the patient, the device being controlled externally of the patient by endoscopic means. The device may comprise a sewing or stapling device for use in flexible endoscopy, though it is also applicable to devices for use in rigid endoscopy.

Apposition devices of this general type are described in, for example, U.S. Pat. Nos. 5,080,663 and 5,792,153. Those patents disclose a sewing device for passing a suture thread through a tissue fold, which comprises a hollow needle movable between a first position in which it is out of the said tissue fold and a second position in which it passes through the said tissue fold, and a thread carrier adapted to be attached to the thread and being receivable within the hollow needle. The sewing device comprises a body, which defines a cavity within which the tissue fold can be held by means of suction, and the hollow needle is mounted for movement in the body between the first and second positions.

Two particular embodiments are described in the above-referenced U.S. Pat. No. 5,792,153 patent: a single stitch sewing device, and a multiple stitch sewing device. In the single stitch device, the thread carrier is transported by the needle through the tissue as the latter passes from its first position to its second position. When the needle returns to its first position, the thread carrier is left behind in the distal end of the sewing capsule. In the multiple stitch device, the same procedure occurs, but it is followed by a further step in which the hollow needle travels from its first position to its second position, picks up the thread carrier, and returns it. A second stitch may be formed during the next step. The whole sequence of steps is repeated as many times as may be required to form the desired number of stitches.

A variable in the success of keeping tissue joined together is the quality of the surgical knot tied to secure the tissue. It would be desirable to improve the reliability of the suture knot to increase the level of confidence in the procedures performed using the above-mentioned endoscopic devices. To improve the reliability of known methods of securing tissue together, the methods should be improved, or safeguarded with a secondary securement operation. The present invention provides improved methods and devices for joining tissue.

SUMMARY OF THE INVENTION

The present invention provides a method of promoting tissue adhesion between surfaces of tissue. The method comprises injuring an area of the outer surface layer of each tissue surface that is to be joined in order to initiate an injury response resulting in and the formation of scar tissue. After tissue is injured, it undergoes a healing process, a component of which is the formation of scar tissue. The injured tissue surfaces are held in contact during the healing process and new scar tissue formation occurs between the closely held tissue surfaces, causing the surfaces to grow together as one tissue mass. The resulting tissue mass bonds together the previously separate tissue surfaces. The new tissue growth is commonly shared between the two surfaces. After formation of the new tissue, the tissue will remain together without the aid of external tissue apposition means such as a suture, staple or adhesive.

The tissue surfaces may be held in contact during the healing process and scar tissue formation by a variety of mechanisms. Sutures or surgical staples may be used to hold the tissue in contact during the new tissue formation. Suture material may be secured by a surgical knot or by suture lock configured to frictionally engage the suture threads to prevent relative movement between them and the captured tissue. Examples of such suture locks are presented in international application PCT/US01/07349, filed by the assignee of the present invention. That application is incorporated by reference herein in its entirety. Among suture locks disclosed in that application are a two-part ring and plug combination in which the plug is secured into the ring by a friction fit capturing the suture leads between the mating surfaces to secure them. It is preferred that the tissue apposition mechanism, such as a suture or staple, not pass directly through the tissue at the injured areas. The injured tissue areas have been weakened and may be prone to tearing at the site of the suture or staple. The suture or staple should be placed at an area that is adjacent to the injured tissue area, yet situated so that securement of the staple or suture will result in bringing injured areas of tissue into contact.

The injured tissue surfaces need only be held in contact temporarily, during the healing process, until scar tissue has grown between the injured tissue areas. Therefore, the tissue apposition devices need only be temporary. Bioabsorbable sutures, suture clips, staples or other fastening mechanisms may be used in conjunction with this method. Alternatively, other temporary means for joining tissue may be used such as tissue adhesive.

The injury to the tissue surface need only be slight, sufficient to initiate an injury response and the growth of scar tissue. Accordingly, only the outermost surface of the tissue generally should be abraded or destroyed to promote a healing response and tissue adhesion. Such a controlled injury is preferably created by electrical abrasion means such as application of radiofrequency energy to the intended injury location. Radiofrequency energy may be delivered by a variety of available medical devices designed for application of such energy, for example electrophysiology catheters. In the case of internal tissue treatments an electrocautery catheter could be used.

Alternatively, the tissue abrasion means may be integrated in the tissue apposition device that is used to initially capture and secure the tissue folds together. In particular, the abrasion means, such as RF energy emitting plates may be placed on the surfaces of the apposition device that come into contact with the captured tissue folds intended to be joined together. By applying abrasion energy to the surfaces of the tissue, while it is captured and secured by secondary means such as suture or staples, greater accuracy in locating the abrasion area on the tissue so that it will be properly aligned with the abrasion means on the subsequent tissue mounds. Devices and methods directed to the integrated tissue apposition device and abrasion means are disclosed in PCT/US01/06835, also assigned to the assignee of the present invention. That application is incorporated by reference herein, in its entirety. Additional configurations of the tissue apposition device with abrasion means are also disclosed in detail below.

Alternatively, chemical means for abrading the tissue may be used to create the injury. For example, acids or abrasive substances, such as sodium oleate may provide sufficient abrasion to the tissue surfaces to initiate an injury response that will lead to common growth of new tissue between the tissue surfaces. Alternatively, a chemically abrasive substance may be applied in addition to the radiofrequency treatment to enhance the injury created to insure that a healing response is initiated in the tissue. Mechanical means may also be used to abrade the tissue sufficiently to create an injury response. To initiate a mechanical injury, an abrasive surface may be rubbed against the intended injury areas to injure the tissue. The chemical or mechanical abrasion means also may be incorporated directly into the tissue apposition device or applied separately by an independent instrument.

The present method of promoting tissue adhesion is believed to be especially useful in joining together folds or portions of gastric tissue in an endoscopic tissue apposition procedure to treat gastroesophageal reflux disease (G.E.R.D.). U.S. Pat. Nos. 4,841,888, 5,037,021, 5,080,663 and 5,792,153 describe methods and devices for performing endoscopic suturing of tissue to treat G.E.R.D., all of which are herein incorporated by reference in their entirety. Those patents describe endoscopic suturing devices delivered at the distal end of an endoscope through the esophagus to the area slightly below the gastroesophageal junction, the "Z-line" between the esophagus and the stomach where plications of the gastric tissue are to be formed and secured together by sutures or staples.

A potential problem with this procedure is subsequent release of the sutures from the tissue for a variety of reasons. Over time, the suture may tear through the tissue or may loosen if an improper surgical knot had been tied to secure it. Promoting a tissue adhesion between the folds of tissue by the present method helps to insure a permanent bond between the tissue surfaces, regardless of the condition of the suture after a period of time. The present method is useful to help promote tissue adhesion during endoscopic suturing by creating a tissue injury on the tissue surface between the collected folds of tissue. The tissue injury may be applied prior to or after tightening of the suture to bring the folds in close contact.

Although the present invention is especially useful in the above-described G.E.R.D. treatment, other treatments may benefit from application of the method of the present invention. For example, the method may be used to aid in attaching a feeding tube to the small intestine; enclosing intestinal openings in the case of a fistula, repairing esophageal tears or suturing tissue sites of localized bleeding.

It is an object of the present invention to provide a method of promoting tissue adhesion that utilizes localized tissue injury to initiate a healing response and scar tissue formation to bond tissue surfaces together.

It is another object of the invention to provide a method in promoting tissue adhesion to hold folds of tissue on the gastric surface of the stomach to treat G.E.R.D.

It is another object of the invention to provide a method in promoting tissue adhesion that may be accomplished endoscopically at a remote internal treatment site.

It is another object of the present invention to provide a method of promoting tissue adhesion that uses radiofrequency energy to injure the tissue in order to initiate a healing response that promotes new tissue growth between adjacent tissue surfaces that are held in contact by a tissue apposition mechanism.

It is another object of the invention to provide a tissue apposition device with integrated tissue abrasion means.

It is another object of the invention to provide a method of joining tissue folds together using a tissue apposition device with integrated tissue abrasion means to abrade the tissue that is to be joined.

BRIEF DESCRIPTION OF THE DRAWINGS

The foregoing and other objects and advantages of the invention will be appreciated more fully from the following further description thereof, with reference to the accompanying diagrammatic drawings wherein.

DESCRIPTION OF THE ILLUSTRATIVE EMBODIMENTS

The present invention provides a method for promoting tissue adhesion between separate tissue surfaces. As mentioned above, the method is useful for external or internal tissue regions but may be especially useful in endoscopic procedures such as the endoscopic suturing of gastric tissue to treat G.E.R.D. U.S. Pat. Nos. 4,841,888, 5,037,021, 5,080,663 and 5,792,153 describe an endoscopic suturing system and methods with which the present invention is useful or may be used. Those patents are incorporated by reference herein, in their entirety. A brief description of the basic elements of that procedure is presented below and the description of the illustrative embodiment will focus on the method of the present invention as it is used in the endoscopic G.E.R.D. treatment procedure.

Figure 1:
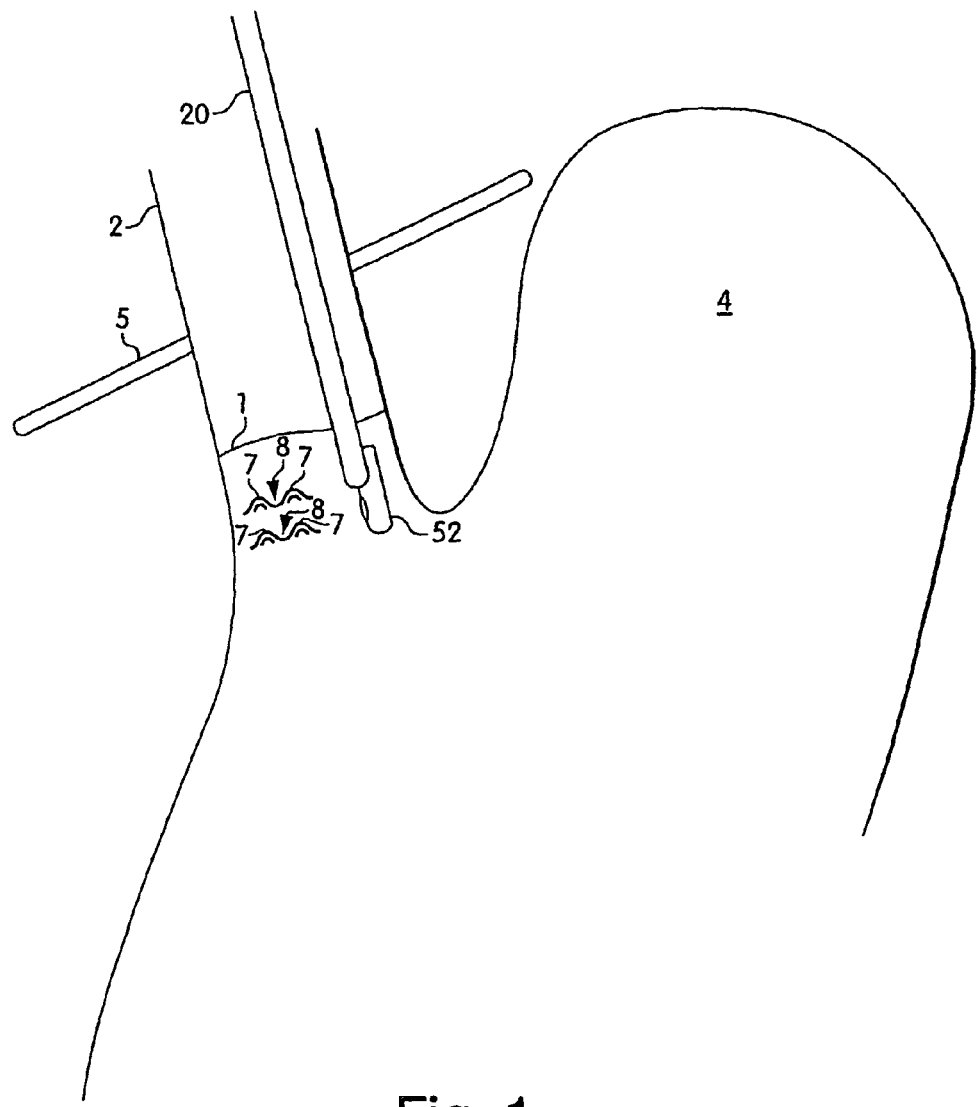
FIG. 1 is a diagrammatic illustration of the region of the gastroesophageal junction between the esophagus and the stomach.

FIG. 1 shows a diagrammatic illustration of the gastroesophageal junction (Z-line) 1 between the esophagus 2 and stomach 4, located below the diaphragm 5. Below the junction, a series of placations 8 are formed, each created by joining together two folds or portions 7 of tissue. The folds 7 of tissue are gathered and joined together by a suturing device 52 mounted at the distal end of an endoscope 20, rather than surgically, to reduce treatment time and trauma to the patient.

Figure 2:
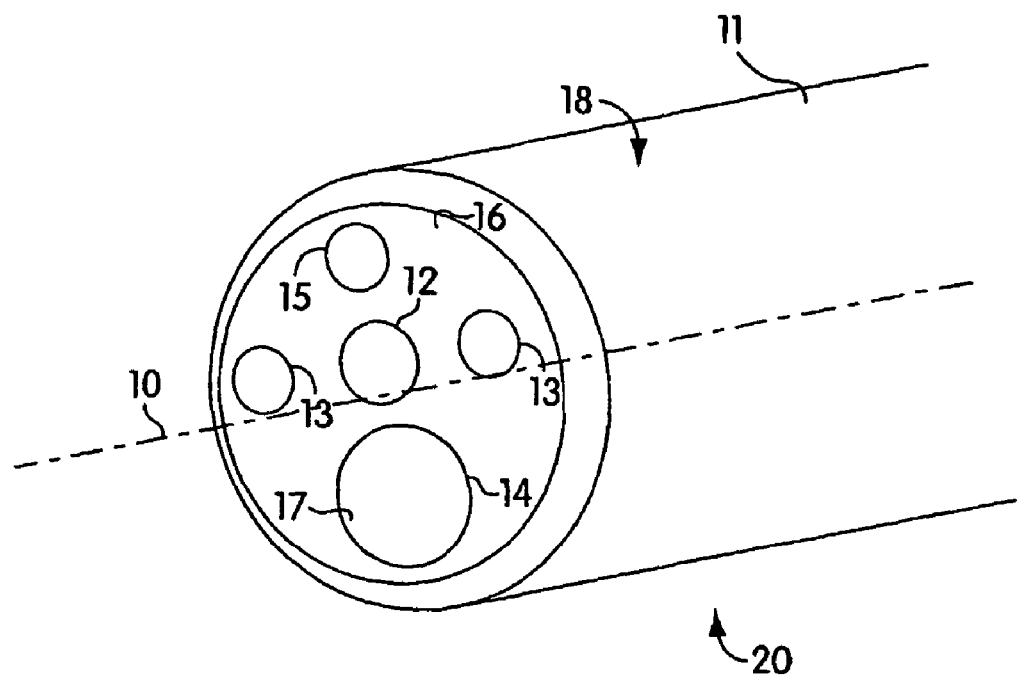
FIG. 2 is a diagrammatic illustration of a distal end of an endoscope.

FIG. 2 shows the distal end 18 of a flexible endoscope 20 with which the present invention may be used. Terminating at a distal face 16 of the endoscope are several channels through which various functions may be performed. Typically, at least one large working channel lumen 14 is provided through which various medical instruments, catheters or accessory control mechanisms may be passed. In the case of viewing endoscopes, a viewing lens 12 is provided on the distal face of the endoscope to permit viewing via optical fiber or digital electronics that extend from the lens to the endoscope to its proximal end. Lights 13 illuminate the treatment site so that it may be viewed through the lens 12. Some endoscopes also have a fluid port 15 through which solution may be passed under pressure to rinse the lens of biological debris during a procedure.

Figure 3:
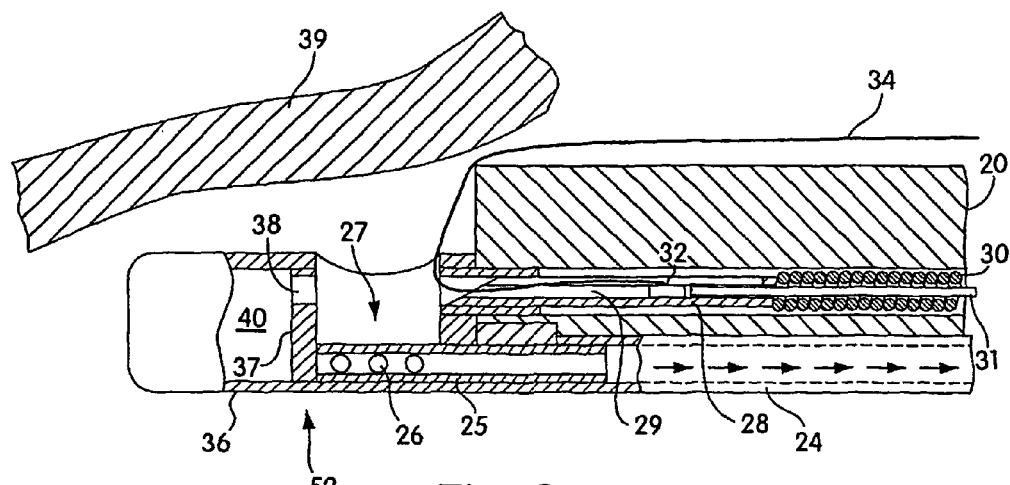
FIGS. 3-5 are partial sectional side views of a prior art endoscopic tissue apposition device placing a suture through a fold of tissue.
Figure 3A:
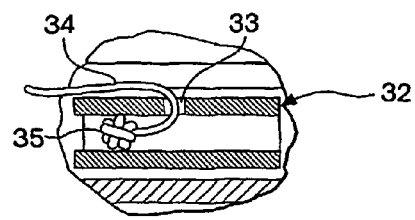
Figure 4:
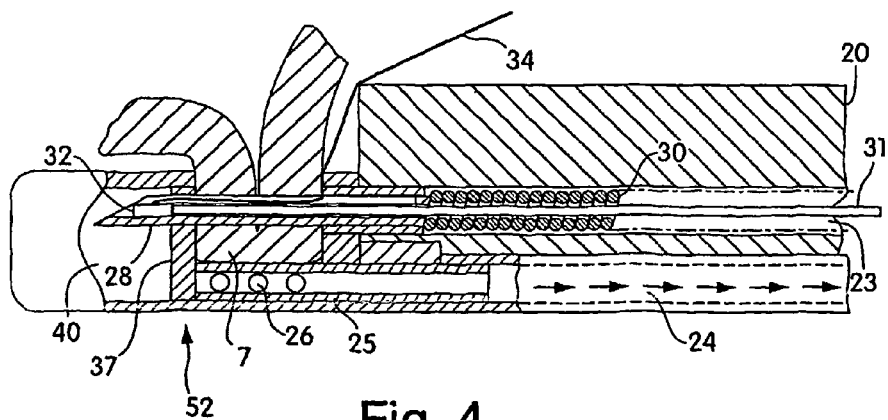
Figure 5:
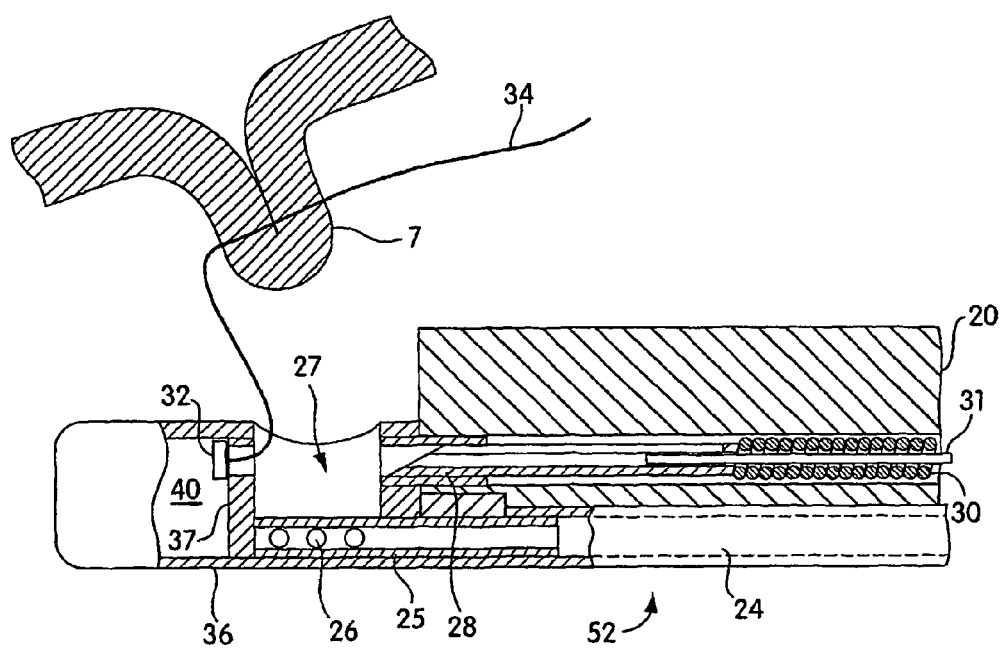

FIGS. 3-5 depict a prior art endoscopic tissue apposition device disclosed in U.S. Pat. No. 5,792,153. FIG. 3 shows the distal end of a flexible endoscope 20, on which a sewing device 52 is attached. As mentioned above, the endoscope is provided with a viewing channel, which is not shown, but which terminates at a lens 12 on the distal face of the endoscope. The endoscope is further provided with a biopsy/working channel 14, and a suction channel 24, the proximal end of which is connected to a source of reduced pressure (not shown). The sewing device 52 has a tube 25, which communicates with the suction pipe 24 and has a plurality of perforations 26 therein. These perforations communicate with an upwardly open cavity 27 formed in the sewing device.

A hollow needle 28 is mounted in the biopsy channel 14, with its beveled tip extending into the sewing device. The needle has a channel 29 extending therethrough. A flexible, wire-wound cable 30 has its forward end attached to the rear of the needle 28, and a center wire 31 runs within the cable 30, along the entire length thereof, and is longitudinally movable with respect thereto. The diameter of the wire 31 is such that it is longitudinally movable within the channel 29 and, in the position shown in FIG. 3, the forward end portion of the wire 31 extends into the rear end portion of the channel 29.

A thread carrier in the form of a tag 32 is mounted in the channel 29. The tag is shown in more detail in the enlarged view, which forms part of FIG. 3. The tag may be hollow and has an aperture 33 extending through the sidewall thereof. As can also be seen in FIG. 3, one end of a thread 34 is secured to the tag by passing it through the aperture 33 and tying in the end of a knot 35 of sufficient size to prevent the thread escaping from the tag.

The sewing device has a hollow head portion 36 defining a chamber 40 therein, with the head portion 36 and the endoscope 1 being on opposite sides of the cavity 27. Between the chamber 40 and the cavity 47 is a wall 37, in which there is formed an aperture 58. The aperture 38 has a diameter that is marginally greater than the external diameter of the needle 28, and is aligned therewith. The clearance between the needle 28 and the aperture 38 must be sufficiently small to prevent tissue from being forced through the aperture and causing the needle to jam. Finally, FIG. 3 shows a portion of the patient's tissue 39, in which a stitch is to be formed.

In operation, suction is applied to the suction pipe 24, and thence, via the perforations 26 in the tube 25 to the cavity 27. This sucks into the cavity a U-shaped fold 7 of the tissue 39, as shown in FIG. 4. The hollow needle 28 is pushed through the U-shaped tissue fold 7 by exerting a distal (leftward) force on the wire-wound cable 30, and the tag 32 is pushed along the channel 29 from right to left, by exerting a leftwards force on the center wire 31. After full advancement of the needle, the tip portion of the needle 28 is on the left-hand side of the wall 37, within the chamber 40 in the hollow head portion 36, and the tag 32, within the channel 29, lies to the left of the wall 37.

Continued distal movement of the wire 31 pushes the tag 32 out of the channel 29 and into the chamber 40. The wire 31 is then withdrawn proximally (rightwardly), followed by the proximal withdrawal of the cable 20, to bring both back to the positions which they occupy in FIG. 3. The suction is then discontinued so allowing the U-shaped tissue fold 7 to be released from the cavity 27. The position is then as shown in FIG. 5. Finally, the endoscope and sewing device are withdrawn from the patient. In so doing, the thread 34 is pulled partially through the tissue fold 7, since the tag 32 is trapped in the chamber 40. The end result is that both ends of the thread are outside of the patient and can be knotted and/or severed as may be appropriate. It should be noted that a multiple stitch embodiment also is disclosed in U.S. Pat. No. 5,792,153.

Figure 6:
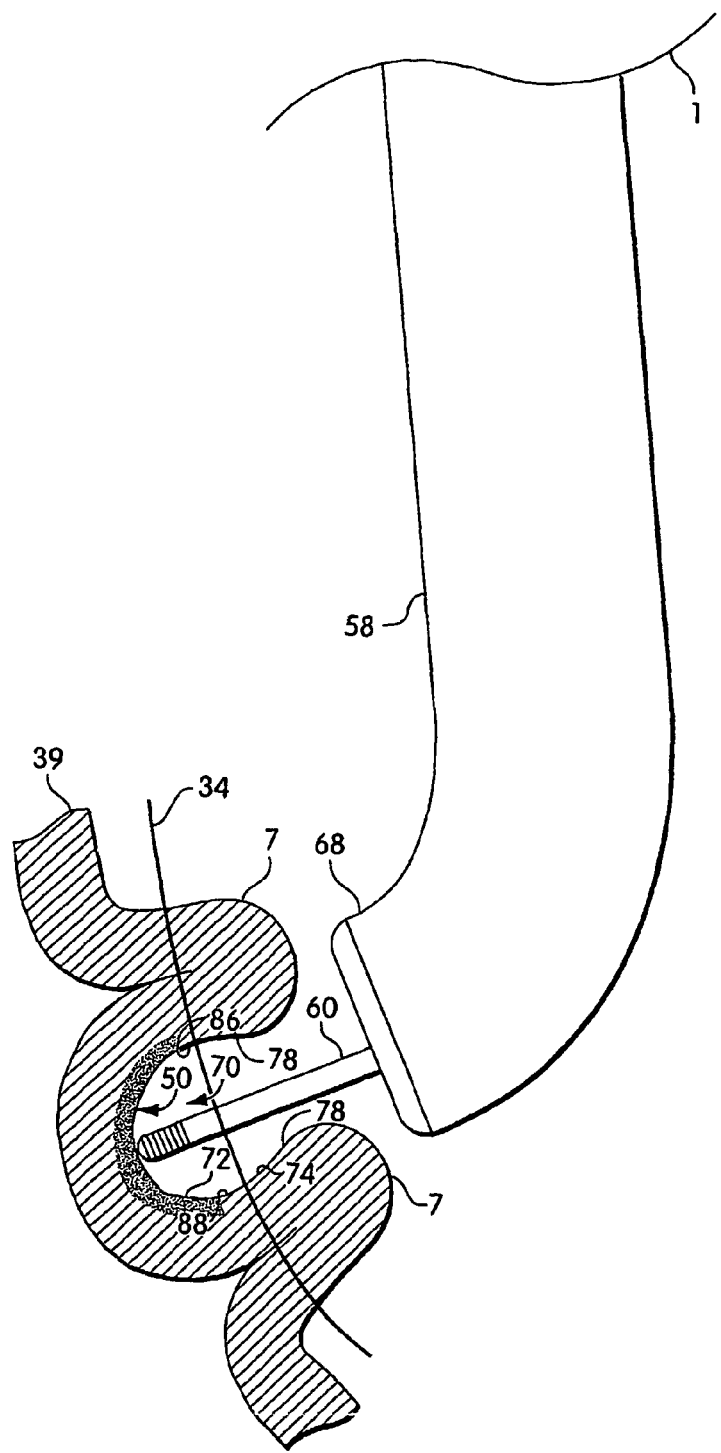
FIG. 6 is a diagrammatic illustration of radiofrequency energy being delivered to injure an area of tissue between two folds of tissue by the use of an endoscopically introduced electrocautery catheter.

FIG. 6 is a diagrammatic illustration of an injury area 50 being created between two folds 7 of tissue that have been captured and penetrated by a suture 34. In a preferred method, after a suture has been placed through the two folds 7, the first endoscope 20, equipped with the suturing system 52, is withdrawn from the esophagus of the patient. Next, a second endoscope 58, without an endoscopic suturing accessory, is then navigated through the esophagus to the Z-line region 1 and site of the tissue folds 7 and suture 34. An electrocautery catheter 60 is introduced through the working channel lumen of the endoscope 58 and, after protruding from the distal end 68 of the endoscope, is directed to the area of tissue between the two folds 7. The second endoscope 58 can be a distal viewing endoscope as shown in the figures, or it may be a side viewing type endoscope (not shown) having a side facing distal working channel port through which an electrocautery catheter would exit.

A standard, commercially available electrocautery catheter is suitable for creating the desired injury, such as the Bard Bi-Polar Hemostasis Probe connected externally to a Valley Lab electrosurgical generator available from Bard Interventional Products Division, C. R. Bard Inc., 129 Concord Road, Billerica, Mass. 01821, or a Gold Probe, bicap probe using an Endostat II generator available from the Microvasive Division of Boston Scientific Corporation, 480 Pleasant Street, Watertown, Mass. 02172. Because a bi-polar type electrocautery probe delivers energy only to a shallow depth of tissue, it is preferred for creating the desired tissue injury of only the outer-most tissue layer or mucosal layer. A mono-polar type probe would not be as suitable for creating the desired shallow injury because it delivers destructive energy more deeply below the tissue surface. The energy applicator at the distal tip of the catheter is directed to the appropriate tissue site by viewing the catheter movement through the endoscope. Directional control of the catheter is accomplished by controlling the distal tip 68 of the endoscope. Additionally, an electrocautery catheter may have a precurved distal tip to aid in navigation after it exits the endoscope. Additionally, a side viewing endoscope offers further directional control over a catheter exiting through the distal port of its working channel by the operation of a movable elevator to affect lifting and angling of the catheter shaft as it exits the endoscope.

As mentioned above, the tissue injury area 50 is preferably positioned between the two tissue folds 7. The area between the folds 7 forms a U-shaped trough 70 when the folds are partially gathered and brought together. Preferably, injury is produced along the bottom of the trough 72, extending partially up the opposing surfaces 86 and 88 on the sides 74 of the trough. However, the injury area 50 should not be extended to include the suture penetration points 78 of the tissue. Creation of the tissue injury by destruction of the mucosal layer weakens the tissue. Tissue that has been injured and contains a suture would be more susceptible to tearing under the motion and concentrated stress of the suture at the penetration points 78.

The injury created by the electrocautery catheter should only affect the mucosal layer of the gastric tissue and should be of a magnitude sufficient to initiate an injury response in the tissue to promote scar tissue growth. Using radiofrequency electrocautery, with a bi-polar probe, it has been found that the desired injury level can be achieved by applying bicap cautery in an approximate range of 25 to 50 watts for an approximate time period of between 2 to 6 seconds.

Alternatively or supplementally, chemical abrasion means may be used to cause injury area on the surface of the tissue. Abrasive or corrosive substances such as sodium oleate may be applied to the desired injury area to chemically abrade the mucosal layer of tissue. Alternatively, the chemical substance may be applied after application of the radio frequency energy to help initiate a tissue injury response that will lead to scar tissue formation between the opposing tissue surfaces 86 and 88.

Alternatively, a mechanical element may be used to abrade the tissue to initiate an injury response on the tissue surface between the tissue folds 7. The mechanical means may comprise an abrasive surface at the distal end of a catheter that is rubbed against the surface of the tissue to create an abrasion that will lead to an injury response and scar tissue formation. New scar tissue will form in the injured tissue area 50, which will unite the two opposing tissue surfaces 86 and 88 as one tissue mass once the healing process has become advanced.

Figure 7:
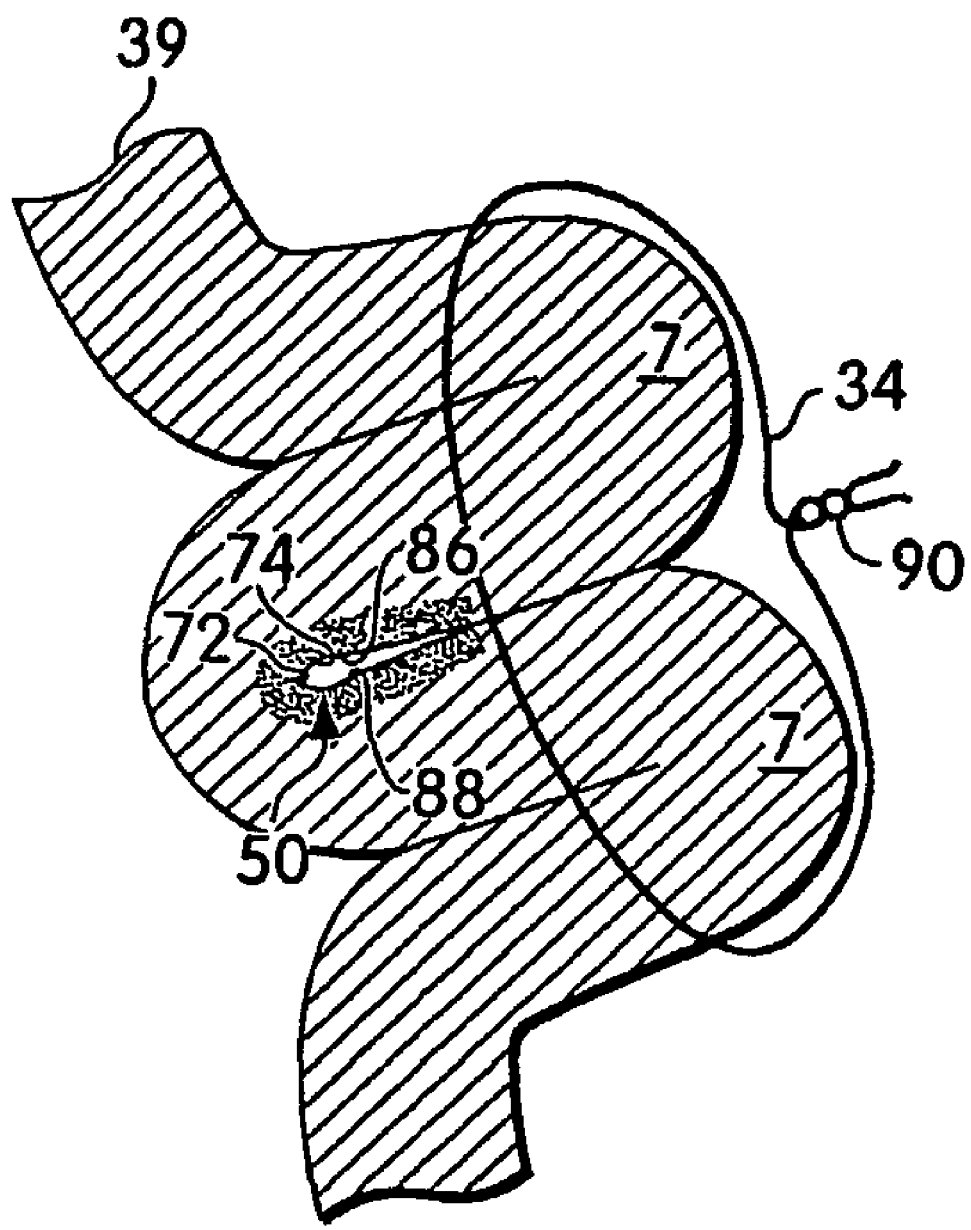
FIG. 7 is a diagrammatic illustration of two folds of tissue being secured together after creation of tissue injury area therebetween.

As shown in FIG. 7 after the tissue injury area 50 has been created, suture 34 may be tightened to draw together the tissue folds 7 and the injured tissue of opposing surfaces 86 and 88 that were created at the bottom 72 and sides 74 of the trough 70. The opposing tissue surfaces 86 and 88 of each tissue fold are thus drawn into contact by the tightening of the suture 34. The suture is then secured by a securement mechanism such as several surgical knots 90. Surgical knots may be run down to the suture site by a knot pusher device attached to the distal end of a endoscope as described in U.S. Pat. No. 6,010,515. Alternatively, the suture may be secured by a suture lock device, such as that described in U.S. Pat. No. 5,584,861. The tissue may also be secured by a staple device such as disclosed in U.S. Pat. No. 5,037,021. The above referenced patents are incorporated by reference herein in their entirety.

Figure 8:
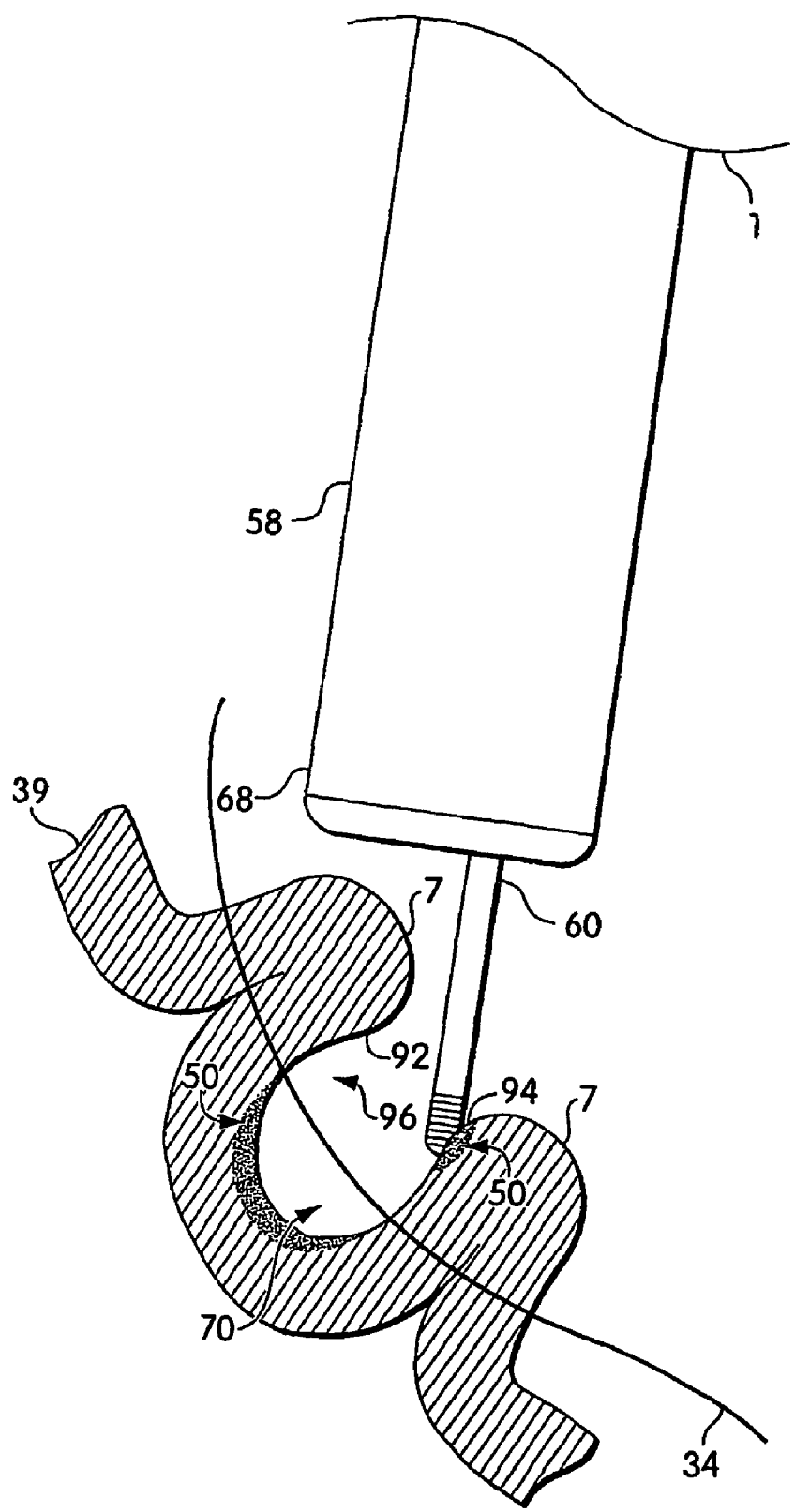
FIG. 8 is a diagrammatic illustration of radiofrequency energy being delivered to injure an area of tissue between two folds of tissue by the use of an endoscopically introduced electrocautery catheter.
Figure 9:
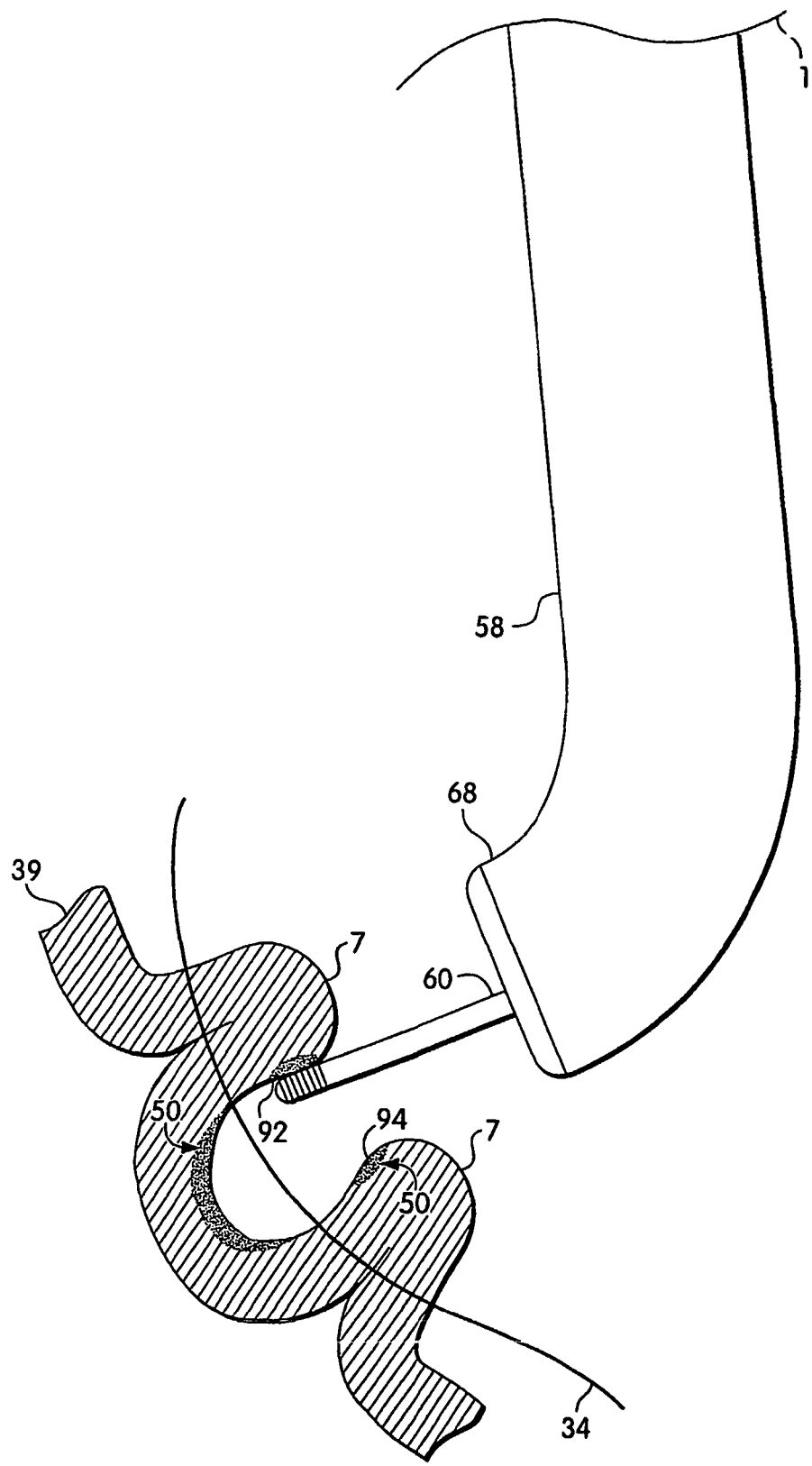
FIG. 9 is a diagrammatic illustration of radiofrequency energy being delivered to injure an area of tissue between two folds of tissue by the use of an endoscopically introduced electrocautery catheter.

As shown in FIGS. 8 and 9, after the opposing surfaces 86 and 88 located at the bottom 72 and sides 74 of the trough 70 has been abraded, opposing surfaces 92 and 94 at the top 96 of the trough 70, above the suture penetration points 78, may be abraded to provide additional tissue adherence between the tissue surfaces.

Figure 10:
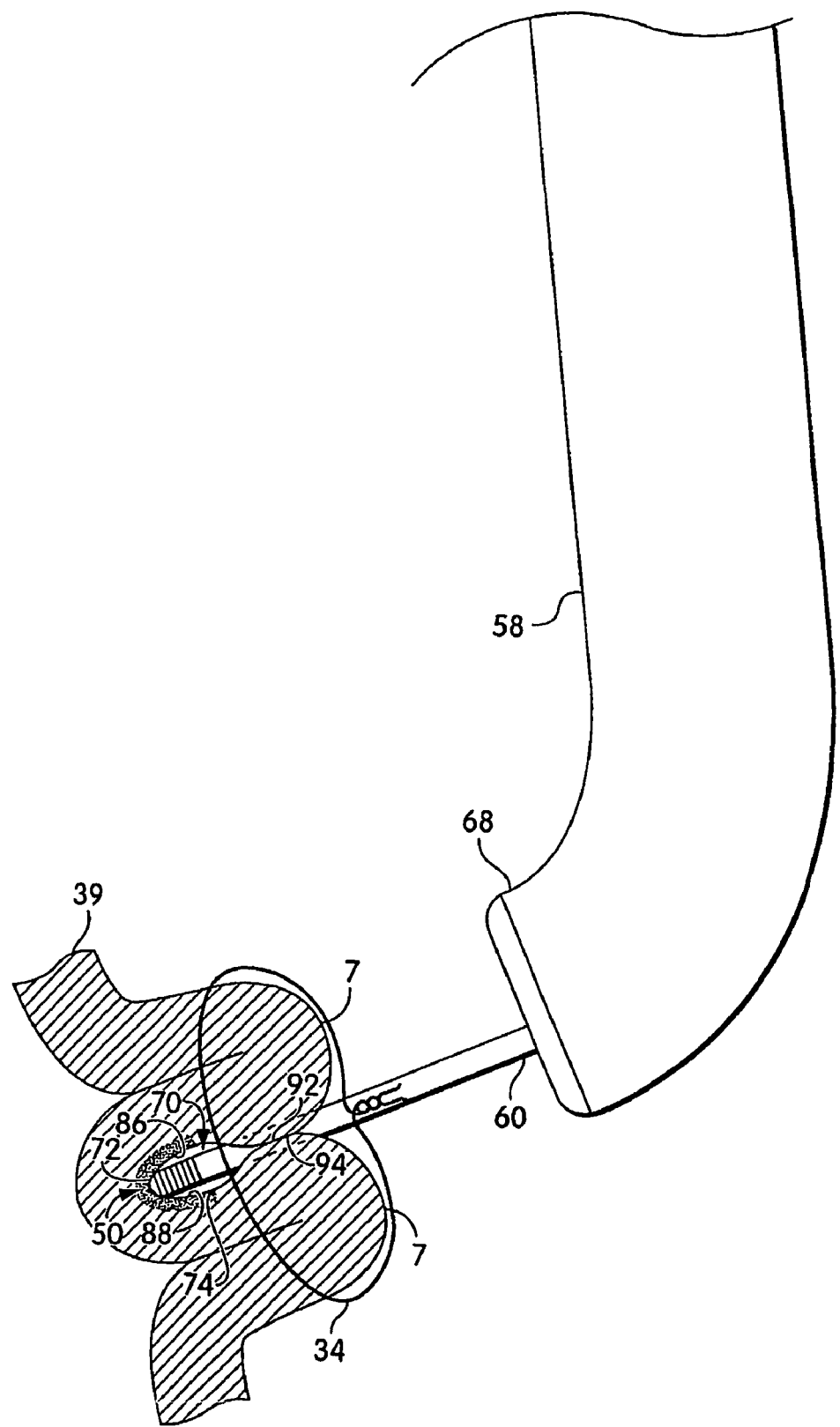
FIG. 10 is a diagrammatic illustration of radiofrequency energy being applied to create an injured area of tissue between two folds of tissue that have been tightly secured together in contact by a previously placed suture.

Another preferred method of promoting tissue adhesion between two folds 7 of tissue is shown in FIG. 10. In this method, the suture 34 is tightened to bring the opposing surfaces 86 and 88 and 92 and 94 of the folds 7 into contact before the tissue injury area 50 is created by the electrocautery catheter 60. After the suture 34 is tightened, the electrocautery catheter 60 is navigated to become wedged between the tissue folds 7 in the trough 70. Once residing in the trough, radio frequency energy is applied to the surrounding tissue surfaces of the bottom 72 and the sides 74 of the trough.

It should be noted that FIG. 10 shows the trough to be a size that permits free access of the distal end 100 of the electrocautery catheter 60 for illustration purposes only. The actual size of the trough 70 after the suture 34 has been pulled tight to secure the tissue folds 7 would be very small or almost non-existent, with opposing surfaces 86 and 88 in contact. However, due to the pliable nature of the tissue, the catheter can still be negotiated between the folds 7 to apply energy to the trough region. An advantage of applying the injury inducing energy after the suture 34 has been tightened is that the surfaces that should be subjected to injury to become bonded will have been clearly defined to the treating physician. Additionally, the snug fit of the catheter in the reduced size trough 70 will insure that the catheter position is correct to deliver its injury creating energy.

Figure 11:
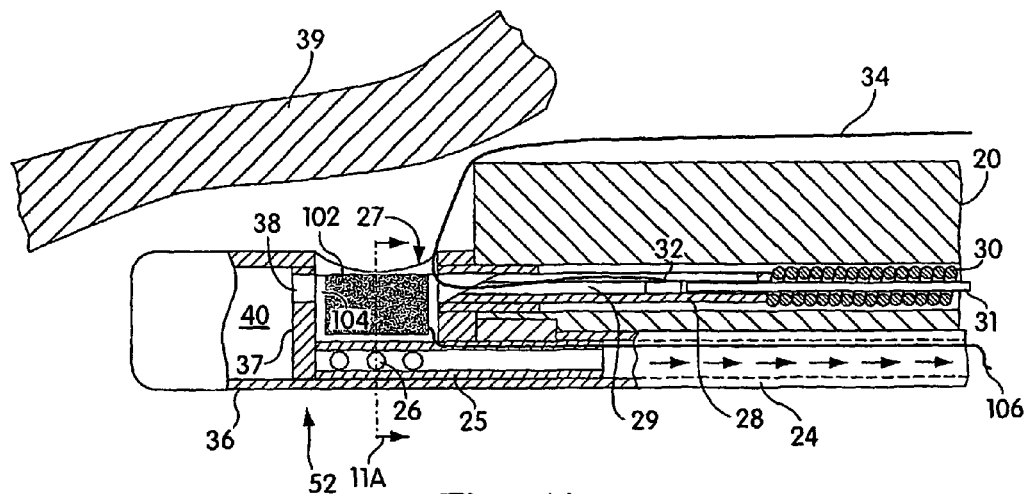
FIGS. 11-13 are partial sectional side views of an endoscopic tissue apposition device placing a suture through a fold of tissue.
Figure 12:
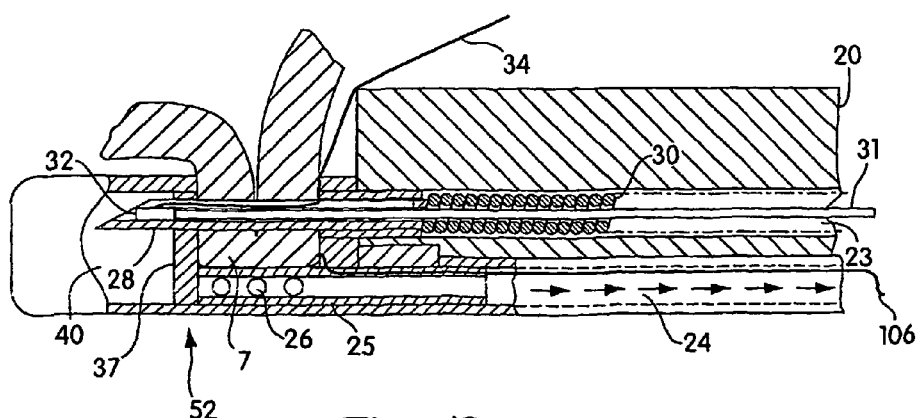
Figure 13:
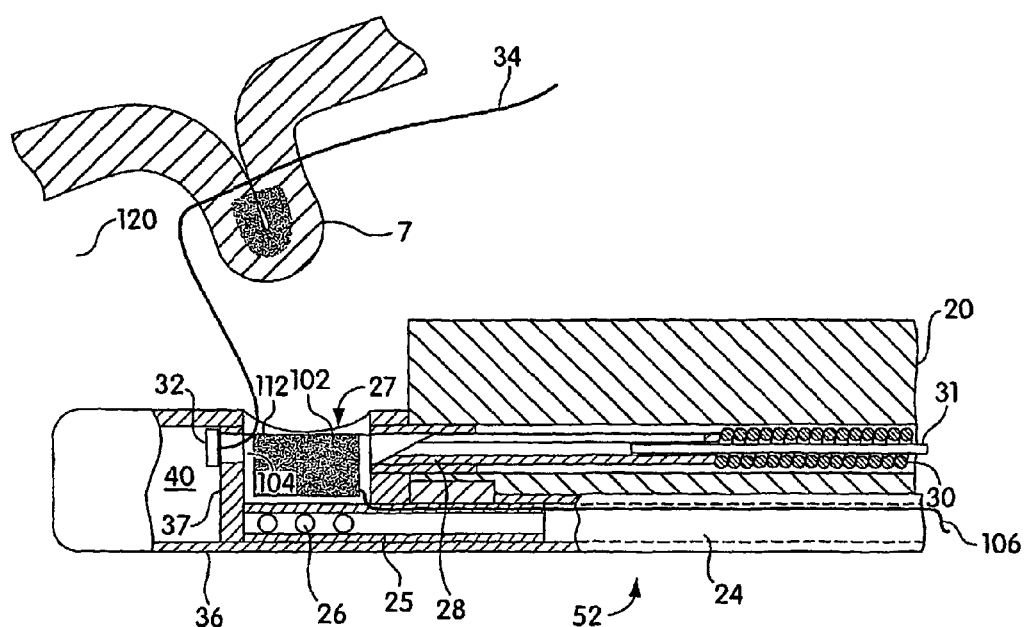

In another aspect of the invention, abrasion means are integrated into the tissue apposition device so that abrasions may be created on the tissue while it is captured by the apposition device 52. A modified tissue apposition device is shown in FIGS. 11-13. The tissue apposition device is modified by the incorporation of tissue abrasion means 102 on at least one tissue contacting surface of the device. The placement of the abrasion means on the apposition device is partially dictated by technical limitations: where the means can be fit onto the device while remaining operable from the proximal end by a user. However, placement of the abrasion means should also be dictated by the desired final arrangement of joined tissue surfaces and the orientation that the apposition device will have relative to that arrangement when it is advanced to the subject area. The abrasion means should be arranged on the device so that injury may be applied to opposing tissue surfaces on the tissue folds that are to be brought together. The injury should be applied to the two tissue surfaces that will be brought into contact with each other. In the example shown in FIGS. 11-13, an abrasion means is located on the sidewalls 104 of the cavity 27 of the apposition device 52. That orientation is suitable for the plication formation described below in connection with FIGS. 14 and 15. However, the abrasion means may be located in various other locations on the apposition device to accommodate a different orientation of the device that may be required to reach a different area of the body or to create a different arrangement of plications. Another consideration in placement of the abrasion means is avoidance of the tissue securement device pathway, such as the needle and suture path through the tissue in the present example. As mentioned above, the suture should not penetrate the area of tissue injury because it is weak and subject to tearing. Placing the abrasion means 102 on the sidewalls 104 of the capsule serves to create injury on the sides of the tissue fold 7 rather than along the suture path, which extends front to back (proximal to distal). Abrasion means may be applied anywhere on the apposition device, on the outside surface or within the cavity 27.

The abrasion means may comprise any of the mechanisms described above: electrical (RF), chemical or mechanical. In FIGS. 11-13 the abrasion means comprises an RF energy emitting plate 102 secured to the sidewall 104 of the suction cavity 27 by such means as adhesive or mechanical fasteners. The RF plate is energized by a wire 106 that extends from the plate, proximally along the endoscope 20 to a RF generator located external to the patient. The wire 106 may extend along the exterior of the scope, with the vacuum tube 24. The penetration point of the wire into the cavity 27 may be sealed to maintain strong suction in the cavity when vacuum is applied.

Because the RF plate 102 conducts electrical energy, it must be insulated from other metal components of the system. The RF plates may be formed from stainless steel and may be coated with a material of greater conductivity such as gold or copper. To prevent electrical conducting to other metal components of the tissue apposition device, the capsule 52 may be formed of a non-conductive material, such as a rigid polymer. Alternatively, the surfaces of the capsule may be insulated from the exposed metal RF plate 102 by coating or lining the surfaces with Teflon or other known insulator materials.

Figure 11A:
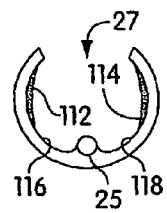
FIG. 11A is a sectional view of the endoscopic tissue apposition device of FIG. 11 taken along the line 11A-11A.

As shown in the sectional view of FIG. 11A, taken along the line 11A-11A of FIG. 11, left and right RF plates 112 and 114 may be provided for left and right sidewalls 116 and 118. The sectional view shows the capsule from the distal end of the scope looking forward, therefore left and right are defined in this discussion from that perspective. The RF plates 112 and 114 are positioned to abrade both sides of a tissue fold 7, but preferably the left and right plates are independently operable so that just one side of the tissue fold can selectively be abraded. The selective abrasion capability increases the flexibility of how plications may be arranged and secured together.

In operation of the apposition device with abrasion means, shown in FIGS. 11-13, suction is applied to the suction pipe 24 and cavity 27, via the perforations 26 in the tube 25 to aspirate a U-shaped fold 7 of the tissue 39 into the cavity, as shown in FIG. 12. The hollow needle 28 is pushed through the U-shaped tissue fold 7 by exerting a distal (leftward) force on the wire-wound cable 30, and the tag 32 is pushed along the channel 29 from right to left, by exerting a leftwards force on the center wire 31. After full advancement of the needle, the tissue is secured in the cavity and will not move appreciably even if it escapes the suction force applied through the cavity 7. In this secured position, the abrasion energy may be applied to cause a tissue injury to the surfaces of the tissue in contact with the RF plates 102. To abrade the tissue, electrical (RF) energy may be applied form the proximal end of the endoscope through the wire 106 to energize the plates 102. Selective activation of the energy between the left and right plates 112 and 114 may be provided. RF energy parameters and times are the same as for the independent RF devices described above.

After application of the abrasion energy the application of the tissue securement mechanism, such as a suture may proceed as was described above for the prior art device in FIGS. 3-5. Continued distal movement of the wire 31 pushes the tag 32 out of the channel 29 and into the chamber 40. The wire 31 is then withdrawn proximally (rightwardly), followed by the proximal withdrawal of the cable 20, to bring both back to the positions which they occupy in FIG. 11. The suction is then discontinued, allowing the U-shaped tissue fold 7 to be released from the cavity 27. As shown in FIG. 13, the resulting tissue fold 7 has an injury area 120 where the abrasion energy was applied. The injury area 120 reflects application of abrasion energy having been applied by right RF plate 114, which cannot be shown in the sectional views of FIGS. 11-13. Likewise, an injury area on the opposite side of injury 120, produced by left RF plate 112, cannot be seen in FIG. 13.

To form plications, with the endoscopic tissue apposition device having abrasion means, two folds of tissue are brought together by tightening of the suture to form a plication. The injured areas 120 on the tissue folds should be aligned to contact each other when the suture is tightened to draw the folds together to form a plication. The series of plications may be formed in a variety of configurations and the most effective configurations for the treatment of GERD is still a subject of investigation at this time. However, several preferred techniques have been established, including the plication configuration described above in connection with the separately applied abrasion devices.

Figure 14:
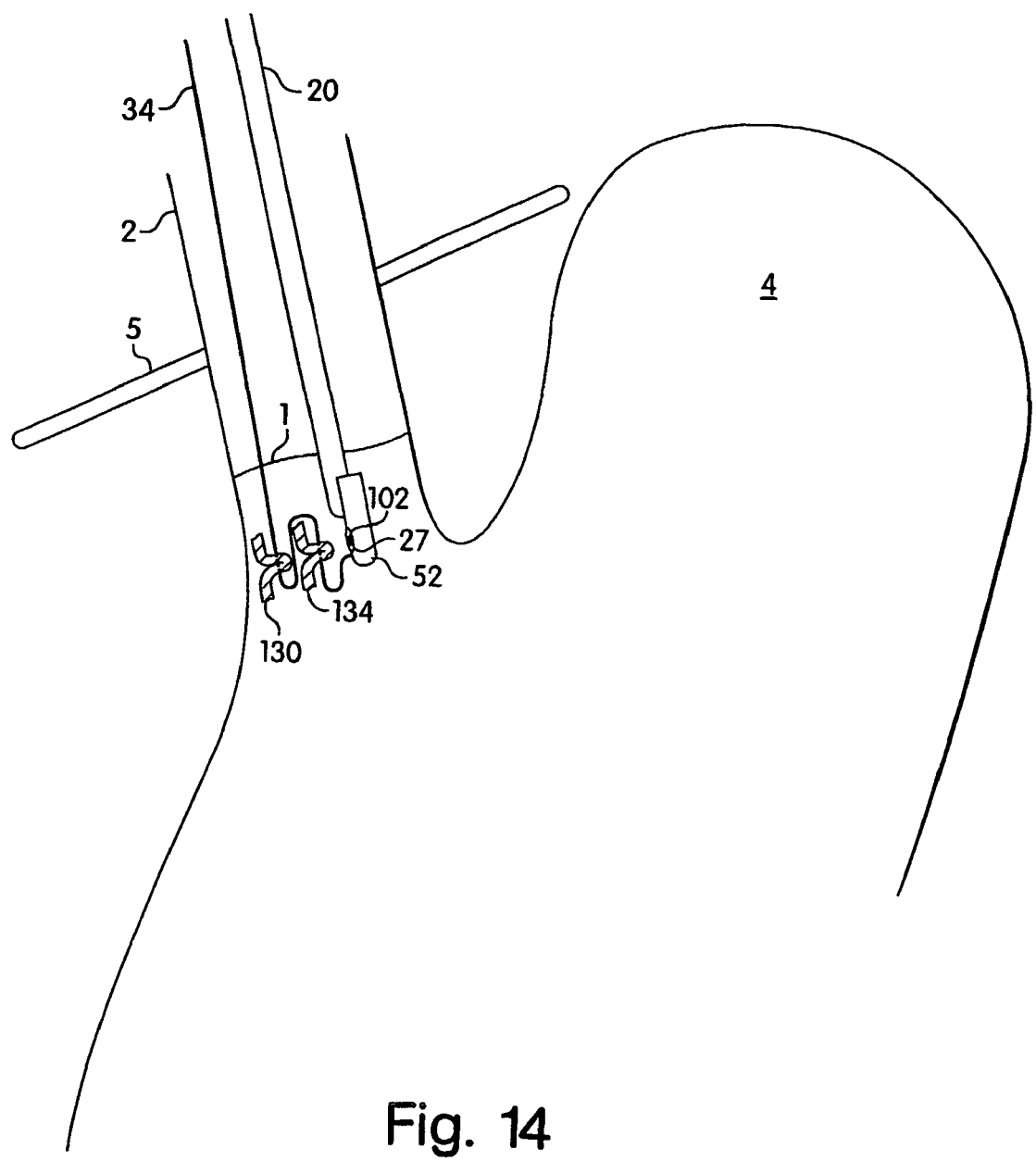
FIG. 14 is a diagrammatic illustration of the region of the gastroesophageal junction between the esophagus and the stomach with an endoscopic tissue apposition device placing sutures through folds of tissue.
Figure 15:
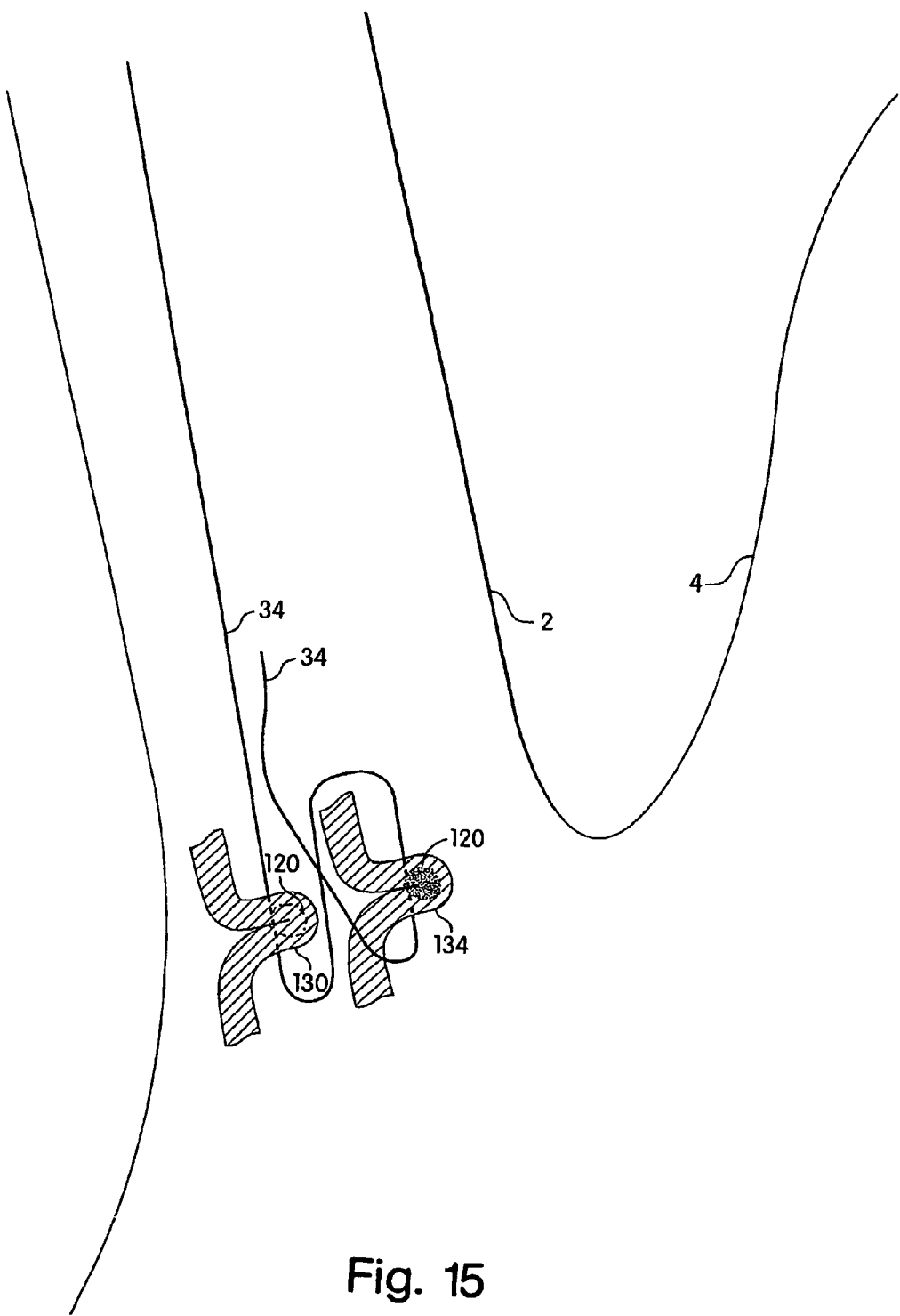
FIG. 15 is a diagrammatic illustration two folds of tissue having opposing injured tissue surfaces that will be brought into contact by the tightening of the sutures.

In another preferred technique shown in FIGS. 14 and 15, tissue folds 7 or folds are captured and sutured at radially spaced locations around the Z-line 1. The tissue capture locations should be at approximately the same longitudinal level. For example the endoscope 20 may be inserted into the esophagus 2 to the proper depth relative to the Z-line for plication formation. The initial insertion depth may be verified visually through the endoscope, and depth placement for subsequent intubations verified visually through the scope or by observation of the endoscope shaft location external to the patient, relative to the mouth.

Next the endoscope is rotated to approximately the one o'clock position and a fold of tissue 130 is captured. Preferably, the needle is advanced through the tissue to hold it in position while abrasion is performed. While the tissue is captured in the cavity, one of the abrasion elements 102 is activated to abrade an area on one side of the tissue fold 130 that will face the next tissue section captured. In FIG. 14, the next tissue fold that will be captured is the 3 o'clock position fold 134. To place an injury 120 on tissue fold 130 that faces fold 134, the left RF plate 112 of the capsule alone should be activated. FIG. 15 shows the injury area 120 on fold 130 in phantom. However, if the apposition device is not configured for independent control of left and right RF plates, both sides of the tissue fold may be abraded. The side of the fold that will not be brought into contact with another fold of tissue will heal without adverse consequence. After the abrasion is created, the suturing procedure may be completed to maintain the tissue fold configuration: the suture is advanced through the needle and tissue fold, needle is withdrawn from the tissue and vacuum is discontinued to release the tissue.

Next, a second tissue fold 134 is captured to be joined to the first tissue fold to form a plication. To capture a second, adjacent fold, the endoscope 20 and suturing capsule 52 may be withdrawn outward from the patient and the suture lead reloaded into the needle for another suture delivery through the second tissue fold located adjacent to the first captured tissue fold. The endoscope is again advanced down the esophagus to a depth equal to that of the first tissue capture. The scope is rotated to the 3 o'clock position to be radially adjacent to the first tissue fold. A tissue fold 134 is aspirated into the cavity 27 and the needle is advanced through the fold to secure it. An abrasion area 120 is created on the side of the tissue fold facing the first tissue fold by activating the right RF plate 114. After the abrasion is created, the suture may be passed through the needle and the tissue fold, needle withdrawn, aspiration discontinued and tissue released. With the two adjacent tissue folds secured by sutures and having facing abrasions, the suture leads 34 may be tightened to draw the tissue folds together with the facing abrasions 120 coming into contact. When the sutures are tightly secured by surgical knot or suture lock. The abrasion areas will be maintained in contact and will heal together, permanently joining the surfaces of the tissue folds.

It should be understood however, that the foregoing description of the invention is intended merely to be illustrative thereof and that other modifications, embodiments and equivalents may be apparent to those who are skilled in the art without departing from its spirit.

Having thus described the invention what we desire to claim and secure by Letters Patent is:

1. A method of promoting tissue adhesion between tissue surfaces, comprising:
   placing a fastener through tissue having the tissue surfaces;
   after and separate from placing the fastener through the tissue, injuring an area of each tissue surface to be joined to initiate an injury response in the tissue that will result in scar tissue formation;
   placing the tissue surfaces to be joined in contact after injuring the area of each tissue surface to be joined; and
   securing the injured tissue surfaces in contact with the fastener for at least the period encompassing the resulting scar tissue formation.

2. The method of promoting tissue adhesion as defined in claim 1, wherein the tissue surfaces are secured in contact by a suture.

3. The method of promoting tissue adhesion as defined in claim 2, wherein the suture is secured by a knot.

4. The method of promoting tissue adhesion as defined in claim 2, wherein the suture is secured by a suture lock device.

5. The method of promoting tissue adhesion as defined in claim 1, wherein the injury destroys the mucosal layer of the affected areas of tissue.

6. The method of promoting tissue adhesion as defined in claim 1, wherein the injury is created by electrical energy.

7. The method of promoting tissue adhesion as defined in claim 6, wherein the energy is radiofrequency energy.

8. The method of promoting tissue adhesion as defined in claim 6, wherein the radiofrequency energy is applied by an electrocautery catheter.

9. The method of promoting tissue adhesion as defined in claim 6, wherein the injury created by the radiofrequency energy is supplemented by application of sodium oleate.

10. The method of promoting tissue adhesion as defined in claim 1, wherein the injury is created by a chemical substance.

11. The method of promoting tissue adhesion as defined in claim 10, wherein injury is created by application of sodium oleate.

12. The method of promoting tissue adhesion as defined in claim 1, wherein the injury is created by mechanical means to abrade the tissue.

13. The method of promoting tissue adhesion as defined in claim 1, wherein the tissue surfaces comprise external tissue of the human body.

14. The method of promoting tissue adhesion as defined in claim 1, wherein the tissue surfaces comprises internal tissue of the human body.

15. The method of promoting tissue adhesion as defined in claim 14, wherein the injury is created between and on facing surfaces of tissue folds previously collected and through which a suture has been passed.

16. The method of promoting tissue adhesion as defined in claim 15, further comprising tightening the suture to draw the tissue folds and injured surfaces together after the injury has been created.

17. The method of promoting tissue adhesion between tissue surfaces as defined in claim 1, wherein the tissue is gastric tissue and the injury is applied to the mucosal layer of the gastric tissue.

18. The method of promoting tissue adhesion as defined in claim 1, wherein the method is performed endoscopically.

19. A method of promoting tissue adhesion between tissue surfaces, comprising:
   collecting tissue with tissue surfaces facing each other;
   placing a fastener through the collected tissue;
   after and separate from placing the fastener through the collected tissue, creating a tissue injury on each tissue surface that faces the other, wherein the tissue injury is sufficient to result in scar tissue formation;
   placing the injured tissue surfaces in contact after creating the tissue injury on each tissue surface; and
   securing the injured tissue surfaces in contact with the fastener for at least the period encompassing the resulting scar tissue formation.

20. A method of promoting tissue adhesion between tissue surfaces, comprising:
   collecting two areas of tissue that are to be joined by adhesion;
   placing a fastener through the collected tissue;
   after and separate from placing the fastener through the collected tissue, creating a tissue injury on the tissue surface of each area, wherein the tissue injury is sufficient to result in scar tissue formation;
   placing the injured tissue surfaces in contact after creating the tissue injury on each tissue surface; and securing the injured surfaces in contact with the fastener for at least the period encompassing the resulting scar tissue formation.

21. A method of promoting tissue adhesion between tissue surfaces, comprising:

collecting a first tissue area into a first fold;

placing a fastener through the tissue in the first fold;

collecting a second tissue area, adjacent to the first tissue area, into a second fold;

placing the fastener through the tissue in the second fold;

after placing the fastener through the tissue of the first and second folds, creating a tissue injury on tissue surfaces of the first and second folds, wherein the tissue injury is sufficient to result in scar tissue formation;

placing the injured tissue surfaces in contact after creating the tissue injury on the tissue surfaces; and securing the injured surfaces in contact with the fastener for at least the period encompassing the resulting scar tissue formation.

* * * * *